(12) United States Patent
Lutz

(10) Patent No.: US 6,366,805 B1
(45) Date of Patent: Apr. 2, 2002

(54) TIME FRAME SYNCHRONIZATION OF MEDICAL MONITORING SIGNALS

(75) Inventor: William J. Lutz, Middleton, WI (US)

(73) Assignee: Viasys Healthcare Inc., Madison, WI (US)

( * ) Notice: Subject to any disclaimer, the term of this patent is extended or adjusted under 35 U.S.C. 154(b) by 0 days.

(21) Appl. No.: 09/320,613

(22) Filed: May 26, 1999

(51) Int. Cl.[7] .................................................. A61B 5/00
(52) U.S. Cl. ....................... 600/544; 600/345; 600/588; 600/559
(58) Field of Search ..................... 600/544–7, 345–350, 600/554–559

(56) References Cited

U.S. PATENT DOCUMENTS

| | | | | |
|---|---|---|---|---|
| 3,809,069 A | * | 5/1974 | Bennett ....................... | 600/544 |
| 4,493,327 A | * | 1/1985 | Bergelson et al. .......... | 600/544 |
| 5,540,235 A | * | 7/1996 | Wilson ........................ | 600/544 |
| 5,755,230 A | * | 5/1998 | Schmidt et al. ............. | 600/544 |
| 6,224,549 B1 | * | 5/2001 | Droughton ................... | 600/554 |

* cited by examiner

Primary Examiner—Robert L. Nasser
(74) Attorney, Agent, or Firm—Foley & Lardner

(57) ABSTRACT

The present invention provides a system and method for establishing a synchronized time frame for signals in a medical monitoring system. In particular, the present invention provides a system and method for synchronizing the time frame of stimulation signals provided by a stimulator to a subject and response signals received by an amplifier device from the subject in response thereto. Thus, the present invention allows accurate display and analysis of the relationship between stimulation and response signals by a monitoring device. Time frame synchronization of stimulus and response signals is achieved using a periodic bus cycle clock signal which is provided by a bus, i.e., an IEEE 1394 bus, connecting together each of the devices in the monitoring system. For example, a time frame synchronized stimulation trigger signal may be generated by a stimulus synchronization circuit including a phase-locked loop for providing a local clock signal synchronized to the periodic bus cycle clock signal, and employing the local clock signal to provide a multi-bit signal indicating a segment during a bus cycle during which the stimulation signal is provided by the stimulator to the subject.

20 Claims, 4 Drawing Sheets

TIME FRAME SYNCHRONIZATION OF MEDICAL MONITORING SIGNALS

FIELD OF THE INVENTION

The present invention pertains generally to medical monitoring equipment, including equipment for providing a stimulus signal to a subject and for monitoring the response of the subject to the stimulus, and more particularly to methods and devices for synchronizing the time frames of the stimulus and response signals for analysis and display.

BACKGROUND OF THE INVENTION

Medical monitoring involves monitoring the body of a subject to determine the state of health of the subject and to detect, identify, and diagnosis changes or abnormalities in the state of the body which may be indicative of problems. Medical monitoring may involve monitoring, for example, the motion of a subject's body, temperature or chemical changes of the subject's body, and/or audible or electrical signals generated by the subject's body. For example, electroencephalography (EEG) is a form of medical monitoring wherein the electrical potentials of the subject's brain are monitored by attaching electrodes to the subject's scalp. In electromyography (EMG), electrical activity generated in the subject's muscles is monitored using surface and/or needle recording electrodes. Medical monitoring may take place when a subject is at rest, in motion, or during the performance of a medical procedure. In some cases, medical monitoring involves monitoring the response of the subject to a stimulus. For example, EEG monitoring may be used to detect the electrical response of a subject's brain to audible, visual, or electrical stimuli. Medical monitoring involving stimulus and response detection may be used in combination with EMG and various other medical monitoring methods as well.

A typical method of medical monitoring involving stimulus and response detection includes connecting a stimulator, e.g., via electrodes, to a subject, and placing monitoring electrodes, or other sensors, on the subject to detect the subject's response to the stimuli provided by the stimulator. The stimulator is controlled by a stimulation controller, which provides a trigger signal to a stimulus generator to deliver stimuli of a desired magnitude, duration, and pattern to the subject. The electrodes or other sensors used to detect the response of the subject to the stimuli are connected to an amplifier device which amplifies the detected physiological response signals. The amplified response signals are, in turn, processed, analyzed, and displayed, typically using a microprocessor based monitor device.

In displaying and analyzing detected physiological response signals, it is important that accurate time frame synchronization between the stimulus and response signals is achieved. Such synchronization is critical to determining, for example, the delay time between the stimulus and the response. Such synchronization may be achieved where a stimulation controller, physiological signal amplifier, and analysis and display monitor system are contained in a signal device controlled by a single microprocessor, or by multiple microprocessors operating off of the same system clock. However, it is often desirable to employ stimulator, amplifier, and monitor devices which are implemented as separate devices, each having their own microprocessor control and system clock. This allows for modularity and separation of the medical monitoring system components. Modularity allows a variety of different stimulators, providing a variety of different types of stimulation, and a variety of different amplifier devices, for detecting a variety of different physiological response signals, to be used in combination with each other and with a given analysis and display monitor device. Separation allows the components of the medical monitoring system to be located remotely from each other. For example, during a medical procedure, it may be desirable to have the stimulator and amplifier devices separated from each other and from the analysis and display monitor device, which may be located in another room or even further from the site of the procedure. This minimizes the chance that the medical monitoring system will get in the way of the procedure, and allows the various medical monitoring system components to be positioned optimally such that information is made available to the appropriate personnel where required.

Where separate stimulator, amplifier, and display and analysis monitor devices are employed, and particularly where such devices are separated by a distance, synchronization between the stimulus and response signal time frames can be very difficult to maintain. Each such device is typically controlled by its own device controller, which is driven by its own local device clock. Even if the various device clocks are initially synchronized, and operate at the same nominal rate, divergence between the system clocks over time is inevitable. If the time frames in which the stimulus signal is applied and the response signals are detected cannot be synchronized, accurate display and analysis of the relationship between the stimulus and response signals is not possible. Currently, synchronization is achieved between independent stimulator, amplifier, and display and analysis monitor devices, each having its own independent device controller and device clock, by connecting the stimulator device to the display and analysis monitor device by a wire, and providing a signal on the wire when a stimulus signal is provided to a subject by the stimulator device. The distance over which such a wire can be run is limited. What is desired is a system and method for establishing a synchronous time frame between separate stimulator, amplifier, and monitor display and analysis devices in a medical monitoring system, wherein each such device may have its own independent device controller and device clock.

A general structure for a high speed serial bus for connecting together multiple devices, along with a protocol for sending data on the bus and for sharing the bus medium, is specified in IEEE standard 1394. (The official name of the standard is "IEEE 1394–1995 Standard for High Performance Serial Bus". It is published by the Institute of Electrical and Electronics Engineers (IEEE). IEEE 1394 has been implemented in commercially available products and sold, for example, under the trade name Fire Wire.) A 1394 bus structure is tree-like, having a "root" device, branching out to logical "nodes" in other physical devices. The root is responsible for certain control functions. The root device is chosen during initialization and, once chosen, retains that function as long as it remains connected to the bus. A 1394 network may include up to 63 nodes, with each node specified by a six-bit physical identification number. Multiple networks may be connected by bridges, to a system maximum of 1,023 busses. Combined, IEEE 1394 allows up to 64,449 nodes in a system with a maximum of 256 TB of memory space per node.

The IEEE 1394 bus structure is very flexible. Devices may be plugged into any available port on the bus. Devices can be hot-plugged, i.e., connected or disconnected while energized. The bus configures itself. There is no need to set address switches, and there are no hard wired addresses.

Every time a node is added to or removed from the network, the bus's topology is automatically reconfigured by the bus protocol. There can, however, be at most 16 hops between any two nodes, and devices may not be connected in such a way as to form loops. To maintain signal quality, standard IEEE 1394 bus cables should stretch no more than 4.5 meters between nodes. Physically, a 1394 bus cable terminates in a six-pin connector. The six pins are connected to a pair of power wires and two twisted-wire signal pairs. Each twisted pair is shielded, as is the entire cable. The power wires, which carry up to 1.5 A at 8.40 V, keep all parts of the bus alive even when some devices connected to the bus are unenergized. They also eliminate the need for an external power cable in some devices.

An IEEE 1394 bus is capable of transmitting large amounts of data very rapidly. The IEEE 1394 standard supports data rates of 100, 200, and 400 Mb/s. Depending on the capabilities of connected devices, one pair of devices can be communicating at 100 Mb/s, while another pair on the same bus exchanges data at 400 Mb/s. Additional data rates of 800 and 1600 Mb/s are proposed as extensions to the IEEE 1394 standard.

The IEEE 1394 protocol makes provision for two data-transfer modes, asynchronous and isochronous. Both handle data packets of varying length. In asynchronous mode, the packets are sent to explicit addresses and acknowledgments are returned. The asynchronous mode works well for traffic that does not require high data rates or precise timing, e.g., some control signals.

The isochronous mode broadcasts variable-length packets to all parts of the bus at regular intervals without acknowledgment. Isochronous operation is divided into time segments called isochronous cycles. An isochronous cycle begins when a bus Cycle Master (any isochronous-capable node, automatically selected during bus initialization) arbitrates for the bus and transmits a special asynchronous data packet, called a Cycle Start packet. Within this packet is the value of the Cycle Master's clock counter. All devices on the bus receive this value, and update their own local bus clock counter value in response thereto, guaranteeing that the bus operates to a common time reference.

An IEEE 1394 bus interface is implemented by way of a conceptual bus framework having three layers, a physical layer, a link layer, and an application layer. The physical layer provides low-level access to the 1394 bus. IEEE 1394 devices may have one, two, or three connectors, each connected to a single physical layer chip. Cable power is typically extracted from the bus and used to power the physical layer chip, thereby maintaining the integrity of the bus while a 1394 connected device is turned off. The physical layer exchanges raw data and system clock signals with a link layer controller chip. The link layer is responsible for properly formatting isochronous and asynchronous data packets for transmission, and buffering incoming packets for processing by the application layer. Typical link layer controller chips provide host interfaces compatible with common microprocessors, PCI busses, and synchronous serial busses. The application layer formats packets for specific data transmission applications. Typically, a DSP or a RISC processor is employed as a host processor to the link chip. In addition, an IEEE 1394 bus includes a bus management system, which operates at all the serial bus layers in each device and performs some general control and housekeeping functions.

SUMMARY OF THE INVENTION

The present invention provides a system and method for establishing a synchronized time frame for stimulator, amplifier, and monitor devices in a medical monitoring system. In particular, the present invention provides a system and method for synchronizing the time frame of the delivery of a stimulus signal to a subject with the time frame of response signals received from the subject via an amplifier device and provided to a monitor device for analysis and display. By synchronizing the time frames of the stimulus and response signals, an accurate determination of the relationship between stimulus and response of the subject may be obtained, thereby improving a medical monitoring system's analysis and display capability.

A medical monitoring system incorporating time frame synchronization in accordance with the present invention may include a stimulator device for providing stimulus signals to a subject, an amplifier device for receiving and amplifying response signals from the subject, and a monitor device for analyzing and displaying response data received from the amplifier device. The stimulator, amplifier, and monitor devices may be implemented as independent modular devices, wherein each such device is controlled by its own device controller, having its own independent device clock. (The amplifier and monitor devices may be combined in a single device.) The independent stimulator, amplifier and monitor devices of the medical monitoring system are connected together via a bus, such as an IEEE 1394 serial bus, which provides a periodic master bus cycle clock signal across the bus to guarantee that the bus operates to a common time reference. In accordance with the present invention, the master bus cycle clock signal provided across the bus is employed to provide a synchronized time frame reference for the stimulator, amplifier, and monitor devices. Multiple stimulator devices, providing various types of stimulation, amplifier devices, for receiving and amplifying various response signals, and monitor devices, for analyzing and displaying the response signals, may be connected together and time frame synchronized in this manner.

A stimulator device employed in a medical monitoring system in accordance with the present invention may include a stimulation controller, a stimulus generator, and a stimulus synchronization circuit, along with a bus interface circuit. The stimulator device is connected to a monitor device and an amplifier device via the bus interface. The stimulation controller provides a stimulation trigger pulse signal to the stimulus generator when a stimulus signal is to be provided to the subject. The stimulus signal may be an audible, visual, or electrical stimulus signal provided to the subject from the stimulus generator, via, e.g., electrodes placed on the subject. The response of the subject to the stimulus is received and amplified by the amplifier device. For example, electrodes may be placed on the subject to pick up EEG or EMG signals, which are received and amplified by the amplifier device. The amplified response signals are provided to the monitor device for analysis and display via the bus interface.

In accordance with the present invention, the stimulation trigger pulse signal provided by the stimulation controller to the stimulus generator is also provided to the stimulus synchronization circuit. The stimulus synchronization circuit generates a time frame synchronized stimulation trigger signal indicating the time when the stimulus signal is provided to the subject in a time frame which is synchronized with the amplifier and monitor devices. The time frame synchronized stimulation trigger signal is time frame synchronized using the master bus cycle clock signal provided by the bus connecting the stimulator, amplifier, and monitor devices together. The time frame synchronized stimulations trigger signal may be provided as a message via the bus interface to other devices on the bus for time frame synchronization of other signals (e.g., response signals) with the stimulus signal.

The stimulus synchronization circuit may include a phase lock loop (PLL) circuit which generates a local stimulus synchronization circuit clock signal that is phase locked to the master bus cycle clock signal provided by the bus connecting the stimulator device to the other system devices. The PLL may include, for example, a phase detector, wherein the, e.g., 8 kHz master bus cycle clock signal, from an IEEE 1394 bus, is compared to a local 8 kHz stimulus synchronization circuit clock signal to determine the phase difference therebetween. The output of the phase detection circuit is related to the phase difference between the master bus cycle clock and local clock signals. This signal is filtered, e.g., using a low pass loop filter, and provided to an oscillator, such as a voltage controlled crystal oscillator, which generates a local stimulus synchronization circuit clock signal which is thus driven by the PLL to be synchronized with the master bus cycle clock signal.

The stimulus synchronization circuit preferably generates a time frame synchronized stimulation trigger signal which indicates a point in time during a bus cycle, i.e., between master bus cycle clock signals, when the stimulation pulse trigger signal is provided from the stimulation controller to the stimulus generator to generate a stimulation signal which is provided to the subject. Since the master bus cycle clock is synchronized throughout the system, i.e., in the stimulator, amplifier, and monitor devices, such a signal provided by the stimulus synchronization circuit may be time frame synchronized with the other signals in the system, such as the physiological response signals received by the amplifier device, and may thus be used to provide accurate analysis and display of the relationship between the stimulus and response signals.

The time frame synchronized stimulation trigger signal may be derived by dividing the bus cycle into several equal segments. For example, the 125 microsecond cycle length of the IEEE 1394 bus may be divided, e.g., into twelve segments. The stimulation pulse trigger signal provided by the stimulation controller to the stimulus generator is employed by the stimulus synchronization circuit to generate the time frame synchronized stimulation trigger signal which indicates during which segment of the bus cycle the stimulation trigger signal was provided and, therefore, the time, in a synchronized time frame, when the stimulus was provided to the subject. This may be accomplished, for example, by dividing the local stimulus synchronization circuit clock signal, which is phase locked to the master bus cycle clock signal by the PLL, into various local clock signals having various frequencies. Selected ones of the various local clock signals are provided as inputs to a multi-bit register. The local clock signals are selected to form a varying multi-bit signal on the multi-bit register inputs which divides the master bus cycle into a plurality of equal segments. The stimulation pulse trigger signal from the stimulation controller is provided as a clock signal to the register, to latch into the register the state of the various local clock signals at the time the stimulation pulse trigger signal is provided to the stimulus generator. Thus, the output of the multi-bit register will be a multi-bit signal corresponding to the segment of the bus cycle during which the stimulus signal was applied. For example, for an IEEE 1394 bus, having a cycle frequency of 8 kHz, local stimulus synchronization circuit clock signals of 48 kHz, 24 kHz, and two signals with a frequency of 8 kHz and a duty cycle of one-third and wherein the active portion of the duty cycle is positioned in the center and at the end of the bus cycle, respectively, may be provided to the inputs of a four-bit register. This effectively divides the 8 kHz bus cycle into twelve equal segments. The stimulation pulse trigger signal from the stimulation controller is provided to the clock input of the multi-bit register. When the stimulation pulse trigger signal is provided, the states of the four local clock signals are latched into the register. The output of the register is thus a four-bit signal corresponding to the segment during the bus cycle at which the stimulation pulse trigger signal was provided. This time frame synchronized stimulation pulse trigger signal may be provided to the stimulator bus interface during the next bus cycle, to thereby provide the signal in a message to the other devices in the medical monitoring system. Since the time frame synchronized stimulation pulse trigger signal is synchronized with the master bus cycle clock signal, which is available to all devices on the bus, the stimulation pulse trigger signal may be time frame synchronized with other signals, including detected physiological response signals, in the medical monitoring system, for analysis and display.

Further objects, features, and advantages of the invention will be apparent from the following detailed description when taken in conjunction with the accompanying drawings.

DETAILED DESCRIPTION OF THE INVENTION

Figure 1:
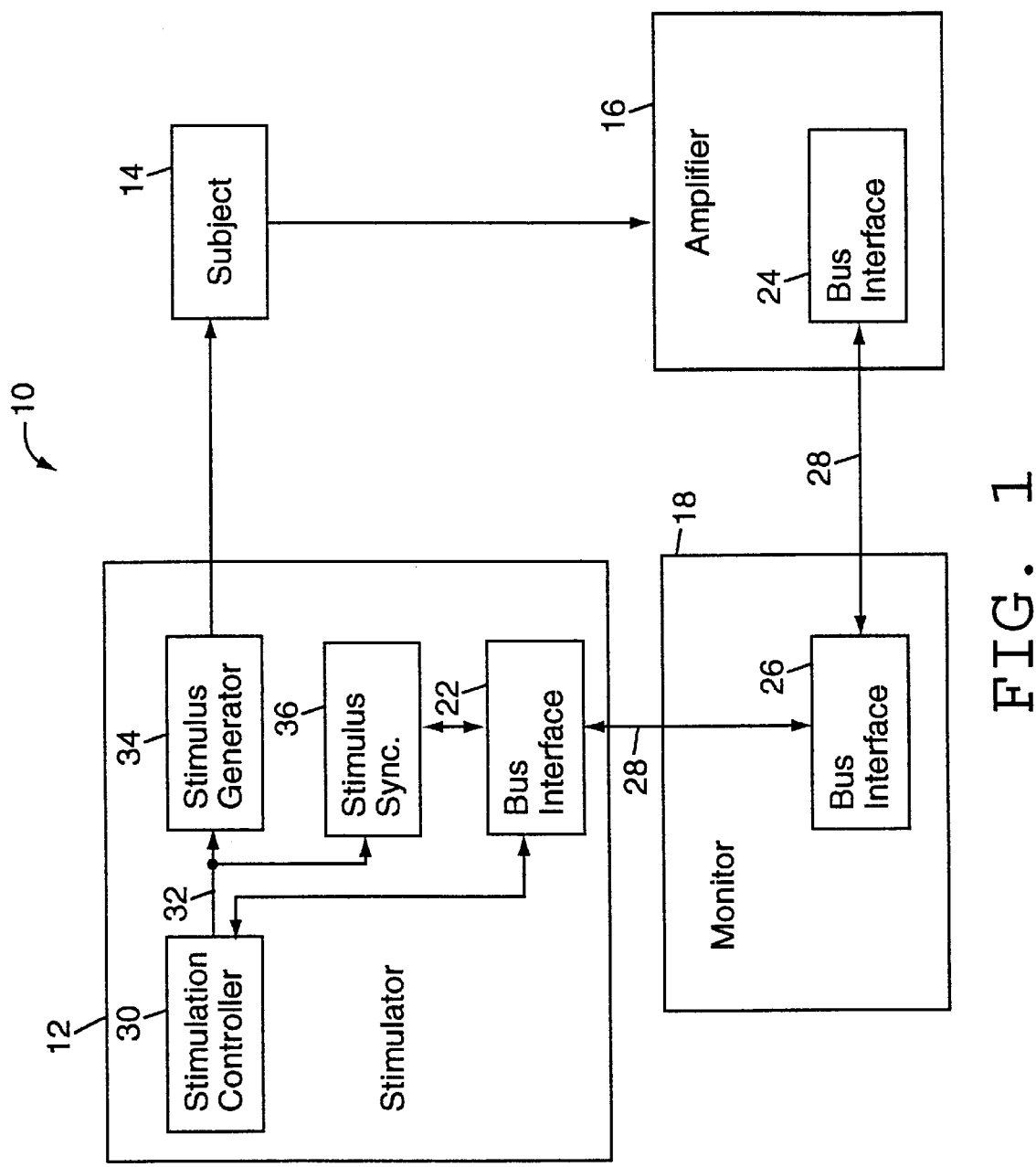
FIG. 1 is a schematic block diagram of an exemplary medical monitoring system employing stimulus and response time frame synchronization in accordance with the present invention.

The present invention provides a system and method for providing time frame synchronization between stimulus and response signals provided, detected, analyzed and/or displayed by a medical monitoring system. An exemplary generic medical monitoring system 10 incorporating the present invention is illustrated in, and will be described with reference to, FIG. 1. The medical monitoring system 10 includes a stimulator device 12, for providing stimulus signals to a subject 14, an amplifier device 16, for receiving and amplifying physiological signals generated by the subject 14 in response to the stimulus, and a monitor device 18, for analyzing and displaying the stimulus and response signals and the relationship therebetween. The present invention is applicable to various medical monitoring systems 10 including standard stimulator 12, amplifier 16, and monitor 18 devices for providing various types of stimulation to a subject 14, and for receiving, analyzing, and displaying various types of physiological responses of the subject 14 thereto. For example, the stimulator device 12 may provide audible, visual, and/or electrical stimulation to the subject 14. An electrical stimulus signal may be provided to the subject 14 from the stimulator 12 via, e.g., electrodes placed at desired positions on the subject 14. The amplifier device 16 may be designed to receive and amplify various physiological signals received from the subject 14. For example, the amplifier 16 may be connected by electrodes to the subject 14 to receive EEG or EMG signals produced by the subject 14 in response to the stimulus provided by the stimulator device 12. The monitor device 18 may include various features for displaying and analyzing the response signals provided by the amplifier device 16. The monitor device 18 may include a display device, e.g., a CRT, and various user interface devices, e.g., a keyboard, mouse, etc. The monitor device 18 is preferably microprocessor controlled, and may be implemented as a computer system programmed for the display, manipulation, and analysis of the response signals provided by the amplifier device 16. In particular, the monitor device 18 may be programmed to display and analyze the relationship between the stimulus signals provided by the stimulator device 12 and response signals received by the amplifier device 16. In order to provide an accurate analysis, the time frames in which the stimulus signals are provided by the stimulator device 12 and in which the response signals are received by the amplifier device 16 must be synchronized. The present invention provides a mechanism for such time frame synchronization.

Each of the stimulator 12, amplifier 16, and monitor 18 devices may be implemented as an independent device, each of which is controlled by its own system controller, e.g., a microprocessor, and each having its own device clock. (Alternatively, two or more of the devices 12, 16, or 18 may be combined into a single unit. For example, the amplifier device 16 and monitor device 18 may be combined into a single device for receiving, analyzing, and displaying physiological response signals.) The stimulator 12, amplifier 16, and monitor 18 devices may be located remotely from each other, e.g., in different parts of a room or building, or even more remotely.

In accordance with the present invention, the stimulator 12, amplifier 16, and monitor 18 devices are connected together via a bus which provides a periodic master bus cycle clock signal to each device on the bus to guarantee that the bus operates to a common time reference. For example, the devices 12, 16, and 18 in the medical monitoring system 10 may be connected by an IEEE 1394 bus. Each device 12, 16, and 18 in the medical monitoring system 10 will, therefore, include a bus interface circuit 22, 24, and 26, respectively. The devices 12, 16, and 18 are connected together by bus cables 28 which are connected between the bus interface circuits 22, 24, and 26. As discussed previously, in an IEEE 1394 bus, the bus cables 28 may connect the devices 12, 16, and 18 together in any topology, provided that the devices are not connected together in such a way as to form a closed loop. As also discussed previously, each bus interface circuit 22, 24, and 26 in the IEEE 1394 topology includes three conceptual layers, a physical layer, a link layer, and an application layer. The physical layer provides low-level access to the 1394 bus. The link layer is responsible for properly formatting data packets for transmission, and for buffering incoming packets for processing by the application layer. The application layer formats packets of data for specific applications. The application layer may be implemented in the microprocessor or other controller which controls operation of the stimulator 12, amplifier 16, or monitor 18 device. Establishing an IEEE 1394 bus link between stimulator 12, amplifier 16, and monitor 18 devices in a medical monitoring system 10 will be known to those skilled in the art, with reference to the available reference literature on the subject.

In operation, the medical monitoring system 10 provides a stimulus signal from the stimulator device 12 to the subject 14. The stimulus protocol, i.e., the intensity, duration, and pattern of stimulation, may be established by a user of the system 10 via the monitoring device 18, which protocol is then provided to the stimulator device 12 over the bus connecting the monitor device 18 to the stimulator device 12, or, alternatively, by a user interface provided directly on the stimulator device 12. Physiological response signals produced by the subject 14 in response to the stimulus signal are detected and amplified by the amplifier device 16. The amplified response signals are provided from the amplifier device 16 to the monitor device 18 over the bus. The response signals are displayed and analyzed in the monitor device 18. In order to provide an accurate analysis of the relationship between the stimulus and response signals, the time delay between the application of the stimulus signal and the detection of response signals must be determined accurately. Since each of the stimulator 12, amplifier 16, and monitor 18 devices operate off of their own independent device clock, accurate time frame synchronization cannot be achieved by reference to any one device's clock alone. In accordance with the present invention, the master bus cycle clock, which is provided by the bus to each of the devices, 12, 16, and 18, in the medical monitoring system 10, is employed to achieve time frame synchronization of the stimulus signals provided by the stimulator device 12 and the response signals received by the amplifier device 16.

The stimulator device 12 is controlled by a stimulation controller 30. The stimulation controller 30 may be implemented in a conventional manner, such as using a microprocessor or other programmable control device. The stimulation controller 30 will operate off of its own stimulator device clock, which is independent from the device clocks in, e.g., the amplifier 16 and monitor 18 devices. When it is desired to provide a stimulus signal to the subject 14, the stimulation controller 30 generates a stimulation pulse trigger signal on a line 32, which is provided to a stimulus generator 34. The stimulus generator 34 operates in a conventional manner to generate a visual, audible, or electrical stimulus signal, which is provided to the subject 14 in response to the stimulation pulse trigger signal. The stimulation controller 30 may provide the stimulation pulse trigger signal in response to programmed instructions provided by a user via the monitoring device 18, which instructions are provided from the monitoring device 18 to the stimulation controller 30 via the bus interface 22, or more directly via a user interface provided on the stimulator device 12.

In order to ensure accurate analysis and display of the relationship between the stimulus signals provided to the subject 14 and the response signals received therefrom, the stimulation pulse trigger signal provided from the stimulation controller 30 to the stimulus generator 34 is time frame synchronized to the master bus cycle by a stimulus synchronization circuit 36. The stimulus synchronization circuit 36 receives the master bus cycle clock signal from the bus interface 22 and includes means for generating a local stimulus synchronization circuit clock signal which is synchronized to the bus cycle clock. Since the stimulus synchronization circuit clock is synchronized with the bus cycle clock signal, which is provided to each of the other devices 16 and 18 on the bus, the stimulus synchronization circuit 36 is able to place the stimulation pulse trigger signal in a time frame which is shared by each of the other devices 16 and 18 on the bus.

In an IEEE 1394 bus, for example, a Cycle Start packet, including the value of the master bus clock counter, is distributed to each bus interface 22, 24, and 26 every bus cycle. The stimulus synchronization circuit 36 may provide a multi-bit output signal which indicates a segment during a bus cycle in which the stimulation pulse trigger signal is applied to the stimulus generator 34. This time frame synchronized stimulation trigger signal may be provided to the bus interface 22 of the stimulator device 12 for distribution as a message to the other devices 16 and 18 on the bus during the next isochronous bus cycle. Based on the time frame synchronized stimulation trigger signal, and universal knowledge of the master bus clock counter value, the monitor device 18 may be programmed to calculate the exact time relationship between the stimulus signal provided to the subject 14 by the stimulator device 12 and the response signals received by the amplifier device 16 for display and analysis.

Figure 2:
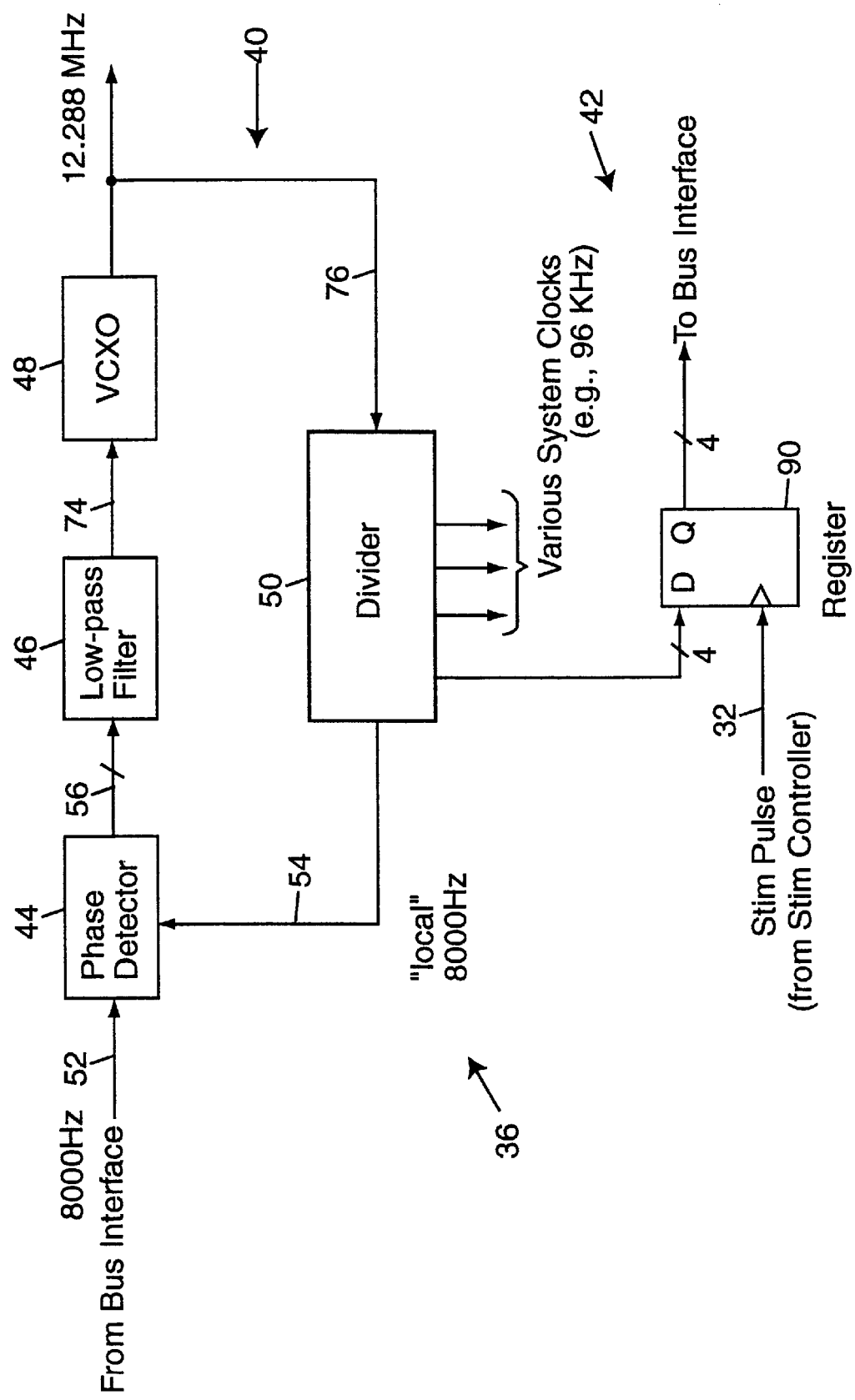
FIG. 2 is a schematic block diagram of an exemplary stimulator time frame synchronization circuit in accordance with the present invention.

An exemplary stimulus synchronization circuit 36 which may be employed in a stimulator device 12 in a medical monitoring system 10 providing stimulus and response time frame synchronization in accordance with the present invention is illustrated in, and will be described with reference to, FIG. 2. The exemplary stimulus synchronization circuit 36 is divided into essentially two functional units, a phase lock loop (PLL) circuit 40 and a circuit 42 for generating a multi-bit time frame synchronized stimulation trigger signal indicating a segment during a bus cycle when a stimulation pulse trigger signal is provided from the stimulation controller 30 to the stimulus generator 34.

The PLL circuit 40 is employed to generate a local stimulus synchronization circuit clock signal which is synchronized with the master bus cycle clock. The PLL circuit 40 preferably includes a phase detector circuit 44, a low-pass loop filter 46, an oscillator circuit 48, and a clock divider circuit 50. The phase detector 44 receives the master bus cycle clock signal on a line 52 from the bus interface 22 and a local stimulus synchronization circuit clock signal from the clock divider 50 on a line 54. For example, in an IEEE 1394 bus, operation is divided into 125 microsecond cycles. A cycle begins when one of the bus interface nodes, designated the bus Cycle Master (any isochronous-capable node, automatically selected during bus initialization), arbitrates for the bus and transmits a special asynchronous packet, called a Cycle Start packet. Within this packet is the value of the Cycle Master's clock counter. All of the bus interface circuits on the bus receive this value and update their own local bus clock counter values, guaranteeing that the bus operates to a common time reference. The 8 kHz master bus cycle clock signal may be provided on the line 52 to the phase detector 44. An 8 kHz local stimulus synchronization circuit clock signal may be provided on the line 54 to the phase detector 44. The phase detector 44 compares the master bus cycle clock signal on line 52 with the local stimulus synchronization circuit clock signal on line 54 to provide an output signal on a line or lines 56 corresponding to the phase difference between the two input signals.

Figure 3:
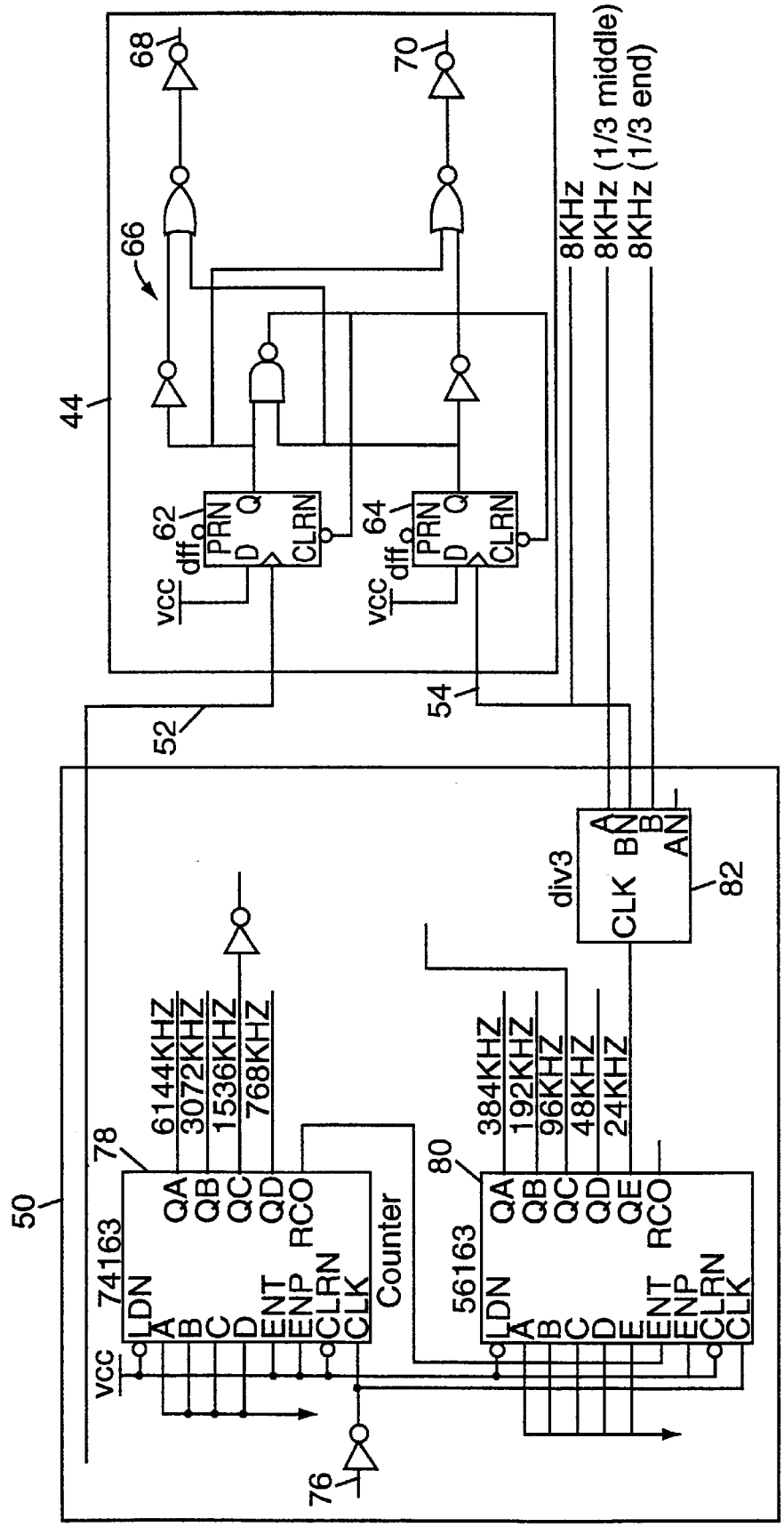
FIG. 3 is a schematic circuit diagram of an exemplary phase detector and clock divider employed in a stimulator time frame synchronization circuit in accordance with the present invention.

The phase detector circuit 44 may be implemented in a conventional manner. An exemplary phase detector circuit 44 which may be employed in the present invention is illustrated in FIG. 3. In the exemplary phase detector circuit 44, each of the bus cycle and local clock signals is provided on a line 52 or 54 to the clock input of a latch 62 or 64, respectively. The output of each latch 62 and 64 goes high in response to a rising edge of the bus cycle or local clock signal provided on lines 52 or 54, respectively. The latch outputs are connected to a logic circuit 66 having two output lines 68 and 70. The logic circuit 66 operates to provide the same output signal (in this case, logic 1) on the output lines 68 and 70 when the output signals provided by the latches 62 and 64 are the same, and different signals on the output lines 68 and 70 during the time between the switching of one of the bus cycle or local clock signals and the other of the bus cycle or local clock signals. For example, when the bus cycle clock signal on line 52 leads the local clock signal on line 54, a logic output 0 is provided on line 68 and a logic output 1 is provided on line 70 starting with the rising edge of the bus cycle clock signal on line 52 and terminating with the rising edge of the local clock signal on line 54. Similarly, if the local clock signal on line 54 leads the bus cycle clock signal on line 52, a logic 1 signal will be provided on line 68 and a logic 0 provided on line 70 starting at the rising edge of the local clock signal on line 54 and terminating at the rising edge of the bus cycle clock signal on line 52. Thus, the two-bit signal provided on output lines 68 and 70 of the phase detector circuit 44 indicates whether or not there is a phase difference between the bus cycle and local clock signals, which clock signal is leading and which clock signal is lagging, and the magnitude of the phase difference (which is determined by the duration during which the output signals on lines 68 and 70 are not equal).

The output of the phase detector circuit 44 is provided to a loop filter circuit 46. The loop filter circuit 46 may be implemented in a conventional manner as a low-pass filter which provides an output voltage signal corresponding to the phase difference between the bus cycle and local clock signals provided on lines 52 and 54.

Figure 4:
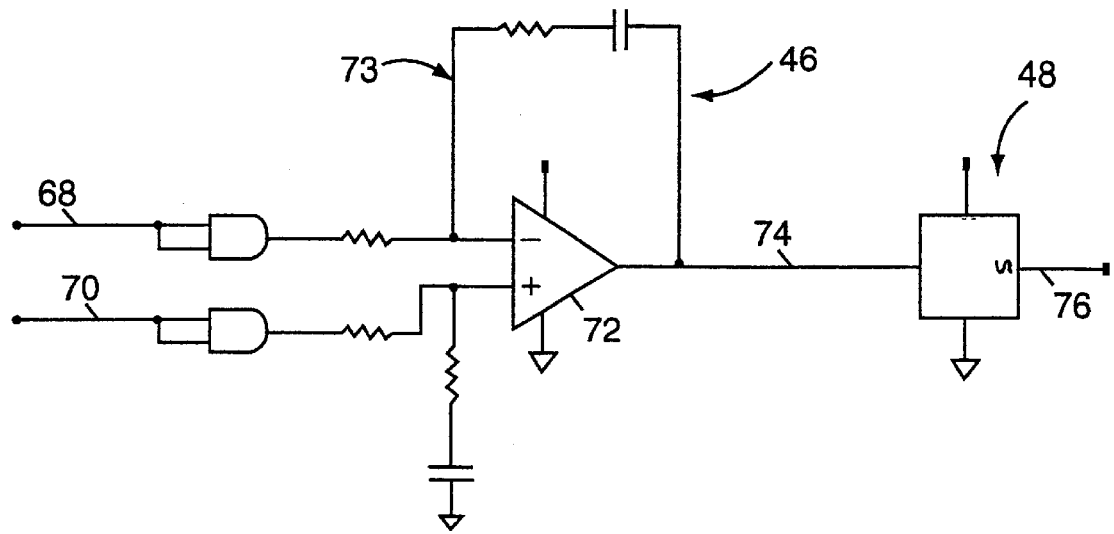
FIG. 4 is a schematic circuit diagram of an exemplary loop filter and voltage controlled crystal oscillator circuit employed in a stimulator time frame synchronization circuit in accordance with the present invention.

A conventional low-pass filter topology may be employed to implement the loop filter 46. An exemplary low-pass loop filter circuit 46 which may be employed in a system in accordance with the present invention is illustrated in FIG. 4. The exemplary low-pass loop filter 46 includes a differential amplifier 72. The output signals provided on lines 68 and 70 from the phase detector circuit 44 are provided to the differential input terminals of the amplifier 72. An integrating circuit 73, including a resistor and a capacitor connected in series, is connected between the output of the amplifier 72 and one of the differential inputs of the amplifier 72. The output of the amplifier 72 and, therefore, of the low-pass loop filter 46 is, therefore, a voltage signal varying in magnitude in response to the phase difference between the bus cycle and local stimulus synchronization circuit clock signals provided on lines 52 and 54.

The output of the low-pass loop filter 46 is provided on a line 74 to an oscillator circuit 48. The oscillator circuit 48 may be implemented in a conventional manner to produce a high frequency local stimulus synchronization circuit clock signal having a frequency which is adjustable in response to a detected phase difference between the local clock signal and the master bus cycle clock signal. For example, the oscillator circuit 48 may be implemented as a voltage controlled crystal oscillator integrated circuit 48, as illustrated in FIG. 4. The exemplary voltage controlled crystal oscillator 48 produces a high frequency clock signal of, e.g., 12.88 MHz, which forms the high frequency local stimulus synchronization circuit clock. The voltage controlled crystal oscillator 48 is responsive to the signal provided from the low-pass loop filter on line 74, to adjust the output frequency of the oscillator 48. In this manner, the local high frequency stimulus synchronization circuit clock signal is synchronized to the bus cycle clock signal in a conventional manner by the PLL 40.

The high frequency local stimulus synchronization circuit clock signal provided by the oscillator circuit 48 cannot be phase compared directly to the lower frequency (8 kHz) bus cycle clock signal provided on line 52 to the phase detector 44. Therefore, the high frequency local stimulus synchronization circuit clock signal is provided from the oscillator circuit 48 on a line 76 to the clock divider 50. In the clock divider 50, the high frequency (e.g., 12.288 MHz) local stimulus synchronization circuit clock signal is divided to derive the local stimulus synchronization circuit 8 kHz clock signal which is provided on line 54 to the phase detector 44, to be phase compared to the 8 kHz bus cycle clock signal from the IEEE 1394 bus interface 22. The clock divider circuit 50 also preferably derives local stimulus synchronization circuit clock signals at various other frequencies from the high frequency clock signal provided by the oscillator circuit 48. The clock divider circuit 50 may be implemented in a conventional manner to derive the various desired local clock signals.

An exemplary clock divider circuit 50 which may be employed in the present invention is illustrated in FIG. 3. The exemplary clock divider circuit 50 includes binary counters 78 and 80 and a divide-by-three counter 82 connected in series. The high frequency local clock signal provided by the oscillator circuit 48 on line 76 is provided as the clocking input signal to the binary counters 78 and 80. Selected outputs of the counters 78, 80, and 82 provide the desired local clock signals of various frequencies. All of the various local clock signals thus derived are synchronized to the local high frequency clock signal provided by the oscillator circuit 48 which, in turn, is synchronized with the bus cycle clock signal provided from the bus interface 22. One of the lower frequency local clock signals provided by the clock divider circuit 50 is the local stimulus synchronization circuit 8 kHz clock signal, which is provided on line 54 to the phase detector 44.

The PLL circuit 36 just described provides various local stimulus synchronization circuit clock signals which are synchronized to the master bus cycle clock signal provided by the bus interface 22. It should be understood that the present invention is not limited to the particular exemplary PLL circuit illustrated and described herein. Other conventional PLL circuits known and used in the art may be employed to derive local stimulus synchronization circuit clock signals of various frequencies which are synchronized with the master bus cycle clock signal provided thereto by the bus via the bus interface 22.

In accordance with the present invention, the stimulus synchronization circuit 36 preferably provides a time frame synchronized stimulation trigger signal which indicates the time at which the stimulation pulse trigger signal is provided from the stimulation controller 30 to the stimulus generator 34, to provide a stimulus signal to the subject 14, in a manner such that the stimulus signal may be time frame synchronized with other signals in the medical monitoring system 10, such as physiological response signals received by the amplifier device 16. The time frame synchronized stimulation trigger signal provided by the stimulus synchronization circuit 36 may preferably include a multi-bit digital signal which indicates a segment of a bus cycle during which the stimulation pulse trigger signal is provided from the stimulation controller 30 to the stimulus generator 34. For example, each 125 μs IEEE 1394 bus cycle may be divided into, e.g., 12 segments. (More or fewer segments may be employed. Preferably, the number of segments selected may be based on the bus cycle frequency such that the "segment" frequency corresponds to the sampling rate of physiological response signals by the system 10.) A four-bit digital signal may be generated by the stimulus synchronization circuit 36 to indicate during which of the 12 segments of the bus cycle the stimulation pulse trigger signal is provided by the stimulation control 30 to the stimulus generator 34. Since the Cycle Master's clock counter is provided each cycle to each device on the bus, the time at which the stimulus signal is provided to the subject 14 from the stimulator device 12 may be derived from the multi-bit time frame synchronized stimulation trigger signal, to thereby synchronize the stimulus signal with, e.g., response signals received by the amplifier device 16.

Figure 5:
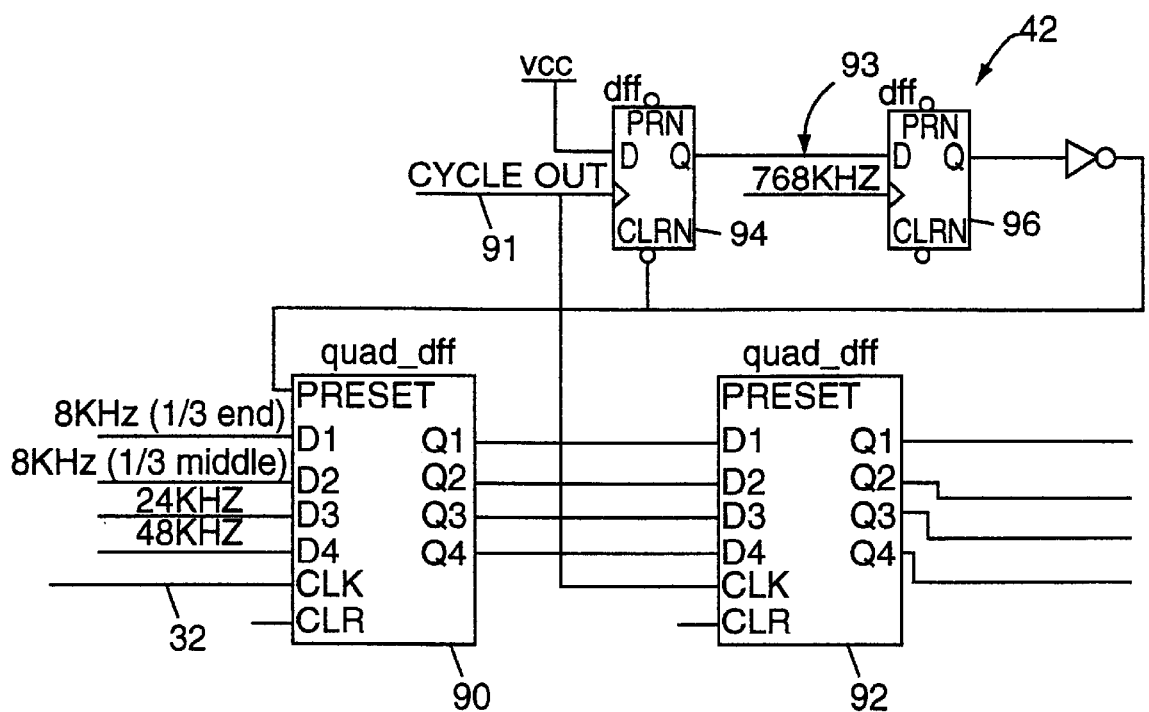
FIG. 5 is a schematic circuit diagram of an exemplary circuit for generating a time frame synchronized stimulation trigger signal indicating a segment of a bus cycle during which a stimulation pulse trigger signal is provided in accordance with the present invention.

An exemplary circuit 42 for generating a multi-bit time frame synchronized stimulation trigger signal which indicates a segment of a bus cycle during which the stimulation pulse trigger signal is provided from the stimulation controller 30 to the stimulus generator 34 is illustrated in, and will be described with reference to, FIG. 5. A four-bit signal indicating the segment of a bus cycle during which the stimulation pulse trigger signal is applied may be derived using a conventional four-bit register 90. Local stimulus synchronization circuit clock signals of, e.g., 48 kHz, 24 kHz, and two signals with a frequency of 8 kHz and a duty cycle of one-third and wherein the active portion of the duty cycle is positioned in the center and at the end of the bus cycle, respectively, may be provided to the inputs of the register 90. It may be seen that these four local clock signals provide a four-bit signal on the inputs to the register 90 which divides the 8 kHz IEEE 1394 bus cycle into 12 equal segments. The local clock signals provided to the register 90 are provided from the clock divider 50 in the PLL 40 of the stimulus synchronization circuit 36. Thus, the local clock signals provided to the register 90 are synchronized to the bus cycle.

At the beginning of a bus cycle, or at the end of a previous bus cycle, a signal is provided to the preset input of the register 90, thereby setting the output of the register 90 to all 1s. During the bus cycle, the local clock signals provided to the input terminals of the register 90 provide a four-bit signal with a value increasing from 0 to 11, thereby dividing the bus cycle into 12 equal segments. The stimulation pulse trigger signal provided by the stimulation controller 30 to the stimulus generator 34 is provided on the line 32 to the clock input of the register 90. Thus, when a stimulation pulse trigger signal is provided from the stimulation controller 30 to the stimulus generator 34 during a bus cycle, a four-bit value between 0 and 11 is latched into the register 90, and provided on the output thereof. This four-bit time frame synchronized stimulation trigger indicates the segment of the bus cycle during which the stimulation pulse trigger signal was provided from the stimulation controller 30 to the stimulus generator 34. If no stimulation pulse trigger signal is provided during a particular bus cycle, the preset value on the register 90, i.e., all 1s, will be provided on the output thereof at the end of the bus cycle.

At the end of the bus cycle, or at the very beginning of the next bus cycle, a cycle-out signal is provided on a line 91, e.g., from the bus interface 22, to the clock input of a four-bit buffer register 92. The inputs of the buffer register 92 are connected to the outputs of the four-bit register 90. Thus, at the end of a bus cycle, the four-bit value indicating whether a stimulation pulse trigger signal had been provided during the previous bus cycle, and, if so, during which segment of the bus cycle the stimulation pulse trigger signal was provided, is latched into the buffer register 92. This multi-bit signal is the multi-bit time frame synchronized stimulation trigger signal. Since the value of the Cycle Master's clock counter is provided to each of the devices on the IEEE 1394 bus, the four-bit signal provided by the stimulus synchronization circuit 36 may be provided as a message, in a conventional manner, to other devices on the bus, such as the monitor device 18, via the bus interface 22, and employed to derive the time that a stimulus pulse is provided from the stimulator 12 to the subject 14, in a time frame synchronized with other signals, e.g., response signals received by the amplifier device 16, in the medical monitoring system 10.

The cycle-out signal provided on the line 91 is also provided to the preset input of the four-bit register 90. The cycle-out signal is preferably provided to the register 90 via a delay circuit 93, which may be formed of series connected latches 94 and 96. The outputs of the four-bit register 90 are thus preset to all 1s between bus cycles, with the delay circuit 93 ensuring that the four-bit output signal of the register 90 is preset only after the value of the signal from the previous cycle has been latched into the buffer register 92 by the cycle-out signal provided on line 91.

It should be understood that the present invention may be employed to provide time frame synchronization of various signals employed in various different types of systems, including medical monitoring systems employing various stimulation, amplifier, and monitor devices, and configurations therefor. Thus, the present invention is not limited to the medical monitoring system 10 illustrated and described by example herein. The present invention may be employed in a medical monitoring system including one or more stimulators for providing visual, auditory, and/or electrical stimulation to a subject, and including one or more amplifier devices for receiving, e.g., EEG, EMG, or other response signals from the subject. Furthermore, the method and apparatus described above for providing time frame synchronization of signals in a medical monitoring system, by providing a multi-bit digital signal indicating the segment of a bus cycle during which a signal occurs, may be applied to signals other than stimulation trigger signals in a medical monitoring system. For example, time frame synchronized response signals may be generated by indicating points in time during a bus cycle wherein specific response signals are received by an amplifier device from a subject. Furthermore, it should be understood that the present invention is not limited to a medical monitoring system having devices connected together by an IEEE 1394 bus, but may be applied to medical monitoring and other systems employing other bus topologies and protocols which provide a periodic bus cycle clock signal guaranteeing that the bus operates to a common time reference.

It is understood that the present invention is not, therefore, limited to the particular embodiments, examples, and applications illustrated and described herein, but embraces all such modified forms thereof as come within the scope of the following claims.

What is claimed is:

1. A medical monitoring system, comprising:
   (a) a stimulator for providing a stimulation signal to a subject;
   (b) an amplifier device for receiving a response signal from the subject;
   (c) a bus connecting the stimulator and the amplifier device together and providing a periodic bus cycle clock signal to the stimulator and amplifier device; and
   (d) time frame synchronization means for employing the periodic bus cycle clock signal to provide time frame synchronization of the stimulation signal with the response signal.

2. The medical monitoring system of claim 1 wherein the stimulator is selected from the group of stimulators consisting of visual stimulators, auditory stimulators, and electrical stimulators.

3. The medical monitoring system of claim 1 wherein the amplifier device is selected from the group of amplifier devices consisting of EEG amplifiers and EMG amplifiers.

4. The medical monitoring system of claim 1 wherein the bus is an IEEE 1394 serial bus and the periodic bus cycle clock signal is a Cycle Start packet.

5. The medical monitoring system of claim 1 wherein the time frame synchronization mean includes a stimulus synchronization circuit for generating a time frame synchronized stimulation pulse trigger signal indicating a segment of a bus cycle during which the stimulation signal is provided to the subject.

6. The medical monitoring system of claim 5 wherein the stimulus synchronization circuit includes a phase lock loop circuit for generating a local stimulus synchronization circuit clock signal synchronized with the periodic bus cycle clock signal.

7. The medical monitoring system of claim 6 wherein the stimulus synchronization circuit includes a clock divider for deriving a plurality of local clock signals of various frequencies from the local stimulus synchronization circuit clock signal.

8. The medical monitoring system of claim 7 wherein the stimulus synchronization circuit includes a multi-bit latch having inputs and outputs and wherein selected ones of the plurality of local clock signals are provided to the inputs of the multi-bit latch to provide a varying multi-bit signal dividing the bus cycle into a plurality of segments, and wherein the varying multi-bit signal on the inputs of the multi-bit latch is latched onto the outputs of the multi-bit latch when the stimulation signal is provided to the subject to provide the time frame synchronized stimulation pulse trigger signal.

9. The medical monitoring system of claim 1 comprising additionally a monitor device for analyzing a relationship between the stimulation signal and the response signal and connected to the stimulator and the amplifier device via the bus.

10. The medical monitoring system of claim 9 wherein the monitor device and the amplifier device are combined into a single device.

11. A method of providing time frame synchronization of medical monitoring system signals, comprising the steps of:
   (a) providing a stimulation signal to a subject;
   (b) receiving a response signal from the subject;
   (c) providing a periodic bus cycle clock signal; and
   (d) employing the periodic bus cycle clock signal to provide time frame synchronization of the stimulation signal with the response signal.

12. The method of claim 11 wherein the step of providing a stimulation signal is selected from the group of steps of providing a stimulation signal consisting of providing a visual stimulation signal, providing an auditory stimulation signal, and providing an electrical stimulation signal.

13. The method of claim 11 wherein the step of receiving a response signal is selected from the group of steps of receiving a response signal consisting of receiving an EEG signal and receiving an EMG signal.

14. The method of claim 11 wherein the step of providing the periodic bus cycle clock signal includes the step of providing an IEEE 1394 serial bus Cycle Start packet.

15. The method of claim 11 wherein the step of employing the periodic bus cycle clock signal to provide time frame synchronization of the stimulation signal with the response signal includes the step of generating a time frame synchronized stimulation pulse trigger signal indicating a segment of a bus cycle during which the stimulation signal is provided to the subject.

16. The method of claim 15 wherein the step of generating a time frame synchronized stimulation pulse trigger signal includes the step of generating a local stimulus synchronization clock signal synchronized with the periodic bus cycle clock signal.

17. The method of claim 16 wherein the step of generating a time frame synchronized stimulation pulse trigger signal includes the further step of deriving a plurality of local clock signals of various frequencies from the local stimulus synchronization clock signal.

18. The method of claim 17 wherein the step of generating a time frame synchronized stimulation pulse trigger signal includes the further steps of providing selected ones of the plurality of local clock signals to inputs of a multi-bit latch to provide a varying multi-bit signal which divides the bus cycle into a plurality of segments, and latching the varying multi-bit signal on the inputs of the multi-bit latch onto the outputs of the multi-bit latch when the stimulation signal is provided to the subject to provide the time frame synchronized stimulation pulse trigger signal.

19. The method of claim 11 comprising additionally the step of analyzing a relationship between the stimulation signal and the response signal.

20. A method of providing time frame synchronization in a medical monitoring system including a stimulator device and at least one other device in the system, comprising the steps of:
  (a) providing a stimulation signal from the stimulator device;
  (b) generating a time frame synchronized signal in the stimulator device indicating when the stimulation signal is provided from the stimulator device in a time frame synchronized with the other device in the system; and
  (c) providing the time frame synchronized signal in a message from the stimuator device to the other device in the system.

* * * * *